(12) United States Patent
Nishiwaki et al.

(10) Patent No.: US 9,682,046 B2
(45) Date of Patent: Jun. 20, 2017

(54) ADSORBENTS FOR ORAL ADMINISTRATION

(71) Applicant: TEIJIN PHARMA LIMITED, Chiyoda-ku, Tokyo (JP)

(72) Inventors: Yasumi Nishiwaki, Hino (JP); Takashi Murakami, Hino (JP); Nobuaki Eto, Hino (JP); Keiichiro Imaizumi, Hino (JP); Akihito Ohtaki, Sunto-gun (JP); Kenji Shimazaki, Sunto-gun (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 14/349,512

(22) PCT Filed: Oct. 5, 2012

(86) PCT No.: PCT/JP2012/075897
§ 371 (c)(1),
(2) Date: Apr. 3, 2014

(87) PCT Pub. No.: WO2013/051680
PCT Pub. Date: Apr. 11, 2013

(65) Prior Publication Data
US 2014/0242147 A1 Aug. 28, 2014

(30) Foreign Application Priority Data

Oct. 7, 2011 (JP) .................................. 2011-222949
Aug. 20, 2012 (JP) .................................. 2012-181466

(51) Int. Cl.
| | | |
|---|---|---|
| *A61K 33/44* | (2006.01) |
| *C01B 31/08* | (2006.01) |
| *A61K 9/70* | (2006.01) |
| *C01B 31/10* | (2006.01) |
| *B01J 20/20* | (2006.01) |
| *B01J 20/28* | (2006.01) |
| *A61K 31/01* | (2006.01) |
| *D01F 9/14* | (2006.01) |

(52) U.S. Cl.
CPC ................ *A61K 9/70* (2013.01); *A61K 31/01* (2013.01); *A61K 33/44* (2013.01); *B01J 20/20* (2013.01); *B01J 20/28004* (2013.01); *B01J 20/2808* (2013.01); *B01J 20/28023* (2013.01); *B01J 20/28066* (2013.01); *B01J 20/28069* (2013.01); *C01B 31/10* (2013.01); *D01F 9/14* (2013.01)

(58) Field of Classification Search
CPC .................. C01B 31/08; A61K 33/94
See application file for complete search history.

(56) References Cited

U.S. PATENT DOCUMENTS

| 4,681,764 A | 7/1987 | Endo et al. | |
|---|---|---|---|
| 7,651,974 B2 * | 1/2010 | Sonobe et al. | 502/418 |
| 2005/0123613 A1 * | 6/2005 | Chen et al. | 424/489 |
| 2005/0150832 A1 | 7/2005 | Tsukamoto | |
| 2005/0173297 A1 | 8/2005 | Toida | |

FOREIGN PATENT DOCUMENTS

| CN | 1229367 | 9/1999 |
|---|---|---|
| CN | 1660350 | 8/2005 |
| CN | 1691948 | 11/2005 |
| CN | 1691949 A | 11/2005 |
| CN | 1897993 | 1/2007 |
| CN | 102140708 | 8/2011 |
| EP | 0914862 | 5/1999 |
| EP | 1500397 A1 | 1/2005 |
| EP | 1547605 | 6/2005 |
| JP | 62-11611 B2 | 3/1987 |
| JP | 2001-164430 A | 6/2001 |
| JP | 2005138038 | 6/2005 |
| JP | 2005-232138 A | 9/2005 |
| JP | 2006036734 A | 2/2006 |
| JP | 2008-55318 A | 3/2008 |
| JP | 2011084454 A | 4/2011 |
| JP | 2011-105545 A | 6/2011 |
| JP | 2011106051 | 6/2011 |
| RU | 2 057 533 C1 | 4/1996 |
| RU | 2 069 560 C1 | 11/1996 |
| WO | 98/03259 A1 | 1/1998 |
| WO | 2005/060980 A1 | 7/2005 |
| WO | 2005062973 | 7/2005 |

OTHER PUBLICATIONS

Forestry Fine Chemicals Technology, vol. 1, p. 465 (2002).
First Examination Report for New Zealand Application IP No. 623528 dated Jan. 22, 2015.
Kynol Products, Kynol® Fibers and Textiles, published at http://www.kynol.de_products.html, 7 pages.
Office Action for Chinese Application No. 2012-80049455.1 dated Dec. 1, 2014.
International Search Report of PCT/JP2012/075897, dated Dec. 18, 2012.
Vladimir N. Anisimov, et al., "Prevention of spontaneous and chemically-induced carcinogenesis using activated carbon fiber adsorbent. I. Effect of the activated carbon fiber adsorbent 'Aqualen' on spontaneous carcinogenesis and life-span in mice", Cancer Letters, 1998, pp. 23-28, vol. 126.

(Continued)

*Primary Examiner* — Nannette Holloman
(74) *Attorney, Agent, or Firm* — Sughrue Mion, PLLC

(57) ABSTRACT

The present invention aims to provide an adsorbent for oral administration comprising ACF that has high adsorption or removal performance by adsorbing or removing toxic substances in the living body greatly and rapidly. The present invention is an adsorbent for oral administration comprising activated carbon fibers for treating or preventing kidney diseases or dialysis complications.

6 Claims, 3 Drawing Sheets

(56) References Cited

OTHER PUBLICATIONS

A.V. Pimenov, et al., "Accelerated Adsorption with Activated Carbon Fiber", Separation Science and Technology, 1995, pp. 3183-3194, vol. 30, No. 16.
Communication dated Mar. 24, 2015 from the Japanese Patent Office in counterpart Application No. 2013-537564.
Communication dated Apr. 13, 2015, issued by the Intellectual Property Office of New Zealand in counterpart New Zealand application No. 623528.
Communication dated May 8, 2015 from the European Patent Office in counterpart application No. 12838141.5.
Communication dated Sep. 2, 2015 from the European Patent Office in counterpart application No. 12838141.5.
Office Action dated Sep. 10, 2015, issued by the Intellectual Property Office of Taiwan in counterpart Taiwanese Patent Application No. 101136852.
Jae-Seung Roh., "Structural Study of the Activated Carbon Fiber using Laser Raman Spectroscopy", Carbon Letters, vol. 9, No. 2, Jun. 2008, pp. 127-130.
Communication dated Jan. 28, 2015, issued by the Intellectual Property Office of Singapore in counterpart Application No. 11201401320Q.
ACF Kuractive Fibers, Kuraray Chemical Co., Ltd., Aug. 3, 2009, section 4.2.
Office Action for Taiwanese Application No. 101136852 dated Mar. 18, 2016.

* cited by examiner

ADSORBENTS FOR ORAL ADMINISTRATION

CROSS REFERENCE TO RELATED APPLICATIONS

This application is a National Stage of International Application No. PCT/JP2012/075897 filed Oct. 5, 2012, claiming priority based on Japanese Patent Application Nos. 2011-222949, filed Oct. 7, 2011 and 2012-181466, filed Aug. 20, 2012, the contents of all of which are incorporated herein by reference in their entirety.

TECHNICAL FIELD

This invention relates to adsorbents for oral administration and, in particular, to a uremic toxin adsorbent for oral administration comprising activated carbon fibers (sometimes referred to hereinafter as "ACFs") as an active component.

BACKGROUND ART

Kidney diseases generally include pathological conditions in the acute and chronic phases, and particularly chronic kidney disease affects about 11% of adults in Japan, the number of which is increasing year by year (Non-patent Literature 1). With decrease in kidney function, chronic kidney disease worsens into uremia due to accumulation in the body such as blood of a harmful toxic substance (a uremic toxin) which is in principle to be excreted from the body. It is thought that uremia itself induces further kidney dysfunction and also does promote progression of chronic kidney disease, although uremia may cause muscle weakness, abnormal sensation, and even hypertension, anemia and cardiac hypertrophy in addition to sleeplessness, headache, bad breath, and appetite reduction (Non-patent Literature 2).

Orally administered adsorbents have attracted attention as an agent that can remove uremic toxins from the body and treat renal and hepatic dysfunctions. Specifically, an adsorbent as disclosed in Patent Literature 1 comprises a porous spherical carbonaceous substance having specific functional groups (hereinafter sometimes referred to as "spherical activated carbon") and can achieve intestinal adsorption and excretion in feces of uremic toxins and precursors thereof (for example, indoleacetic acid) accumulated in vivo, resulting in a reduction in the uremic toxins (for example, indoxylsulfuric acid) in the blood. As agents that can attain such an object, some adsorbents for oral administration comprising spherical activated carbon have been developed so far, and the use of those adsorbents reportedly can suppress kidney injury and delay the induction of dialysis. (Patent Literature 2, Patent Literature 3, Non-patent Literature 3, Non-patent Literature 4, Non-patent Literature 5, Non-patent Literature 6 and Non-patent Literature 7).

Adsorbents for oral administration comprising spherical activated carbon, however, have some disadvantages; these adsorbents have insufficient adsorption performance and are to be administered at high daily doses accordingly, which causes gastrointestinal symptoms, such as constipation and anorexia. In particular, patients with chronic kidney disease, who must control water intake, have to swallow a high dose of 6 g per day of adsorbents for oral administration comprising spherical activated carbon with a small amount of water, which imposes a great strain on the patients.

Presently, hemodialysis enables chronic kidney disease patients with lost kidney function to survive for a longer period, and the advent of dialysis therapy has brought great gospel to many of the patients. However, unless renal transplantation is carried out, the dialysis therapy, which entails chronic complications such as itching and anemia, has to be continued for life and imposes a great mental and physical strain on the patients. It is often reported that accumulation of uremic substances in the body is involved in development of dialysis complications (Non-patent Literature 8), and it is, therefore, a problem how to greatly and rapidly reduce harmful substances that are unable to be removed at all or sufficiently by dialysis from the body.

In addition, other orally administered adsorbents include medicinal carbon (sometimes referred to hereinafter as "powdered activated carbon"). Orally administered medicinal carbon can be used as one of therapeutic approaches to acute drug intoxication that occurs when agrichemicals such as insecticides and herbicides, analgesics and hypnotics are intentionally or accidentally administered in high doses for a short time, which is a pathological condition causing consciousness disorder, respiratory and/or circulatory disorders, or disorders of organs such as kidney and liver. The medicinal carbon can adsorb or precipitate a poison present in the digestive tract to suppress absorption of the poison into the body. The medicinal carbon is required to be administered in an amount of 40 to 60 g per kg of body weight for adults and of 1 g even for children (Non-patent Literature 9), which indicates that adsorption performance of the medicinal carbon as a uremic toxin adsorbent is unclear.

CITATION LIST

Patent Literature

[Patent Literature 1] Japanese Examined Patent Publication No. 62-11611
[Patent Literature 2] Japanese Examined Patent Publication No. 62-29368
[Patent Literature 3] Japanese Examined Patent Publication No. 63-60009

Non-Patent Literature

[Non-patent Literature 1] Japanese Society of Nephrology CKD Shinryo gaido 2009, TOKYO IGAKUSHA
[Non-patent Literature 2] Niwa T., Semin Nephrol., 16 (3), 1996
[Non-patent Literature 3] Shozo Koshikawa et al., Jin to Touseki, 23 (2), 1987
[Non-patent Literature 4] Keizo Koide et al., Rinsho Hyoka, 15 (3), 1998
[Non-patent Literature 5] Tadao Akizawa et al., Jin to Touseki, 45 (3), 1998
[Non-patent Literature 6] Hayashino Y. et al., Diabetes Res Clin Pract. 90 (2),
[Non-patent Literature 7] Nakamura T. et al., Metabolism., 60 (2), 2011
[Non-patent Literature 8] Goto S. et al., Ther Apher Dial., 15 (2), 2011
[Non-patent Literature 9] Kyusei yakubutsu chudoku no shishin, Nihon sogo byoin seishin igakukai Chiryo senryaku kento iinkai, Seiwa shoten, 2008
[Non-patent Literature 10] Masaaki Arakawa et al., Jinzo no saishiniryou, Sentan-Iiryou Gijutsu Kenkyusho, 2001

SUMMARY OF INVENTION

Problem to be Solved by the Invention

An object of the present invention is to provide an adsorbent for oral administration comprising ACFs that have a high adsorption or removal performance by adsorbing or removing toxic substances in vivo greatly and rapidly.
Another object of the present invention is to provide an ACF-containing therapeutic or prophylactic drug for kidney diseases or dialysis complications.

Means for Solving the Problem

The present inventors have diligently researched to seek an adsorbent for oral administration having an adsorption performance far superior to those of adsorbents for oral administration comprising conventional spherical activated carbon, and as a result, have found that an adsorbent for oral administration having an excellent adsorption performance and/or initial rate of absorption can be obtained by using ACFs as an active component.

More specifically, the present invention is as follows:

(1) A uremic toxin adsorbent for oral administration comprising activated carbon fibers as an active component;

(2) The uremic toxin adsorbent for oral administration according to (1), wherein the activated carbon fibers have a micropore volume of 0.1 to 2.0 mL/g;

(3) The uremic toxin adsorbent for oral administration according to (1) or (2), wherein the activated carbon fibers have a fiber length of 15 µm or more and a micropore volume of 0.5 to 1.0 mL/g;

(4) The uremic toxin adsorbent for oral administration according to any one of (1) to (3) for treating or preventing kidney diseases or dialysis complications;

(5) The uremic toxin adsorbent for oral administration according to any one of (1) to (4), wherein the adsorbent is administered at a daily dose of 1 to 3000 mg.

(6) An activated carbon fiber having a cross-sectional diameter of the fiber of 5 to 50 µm, a fiber length of 15 µm or more, a specific surface area as determined by BET method of 1400 to 2700 $m^2/g$, a total pore volume of 0.8 to 1.8 mL/g, and a micropore volume of 0.5 to 1.0 mL/g.

Advantageous Effects of Invention

Compared to conventional adsorbents for oral administration, the adsorbent for oral administration according to the present invention has a higher adsorption performance or a superior initial rate of absorption, and can adsorb harmful toxic substances in vivo rapidly in the intestinal tract and consequently lower the dose. In addition, the adsorbent for oral administration according to the present invention has a low adsorptivity toward high molecular weight compounds such as enzymes that are essential to living organism, and therefore, a sufficient selective adsorptivity. Moreover, the inventive adsorbent becomes easy to swallow because it is significantly small in size compared to conventional adsorbents for oral administration. As mentioned above, the adsorbent for oral administration according to the present invention becomes a superior therapeutic or prophylactic drug for kidney diseases and dialysis complications compared to conventional adsorbents for oral administration.

DESCRIPTION OF EMBODIMENTS

[ACF]

Figure 1:
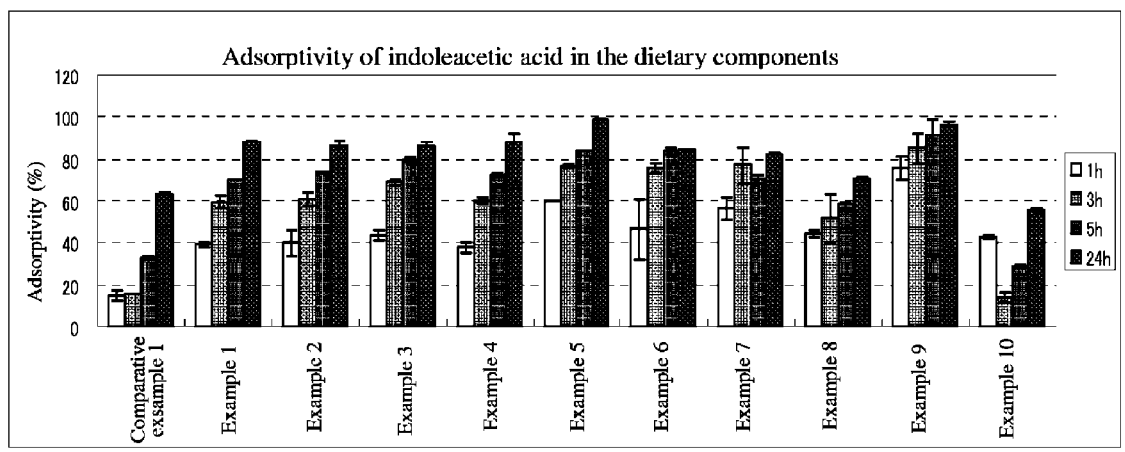
FIG. 1 is a graph showing the adsorptivity of the uremic toxin in the dietary components for Examples.

The ACFs in the present invention, known as activated carbon fibers or fibrous activated carbon, are prepared by curing acrylonitrile-based fibers, phenolic fibers, and fiberized pitch (byproducts from petroleum, coal, coal-tar and the like) by oxidation treatment, followed by activation.

The ACFs have the following properties:

(a) Purification of impurities in the raw material components is done to a high level.

(b) Highly drawn uniaxially in the spinning process, the ACFs have a highly oriented structure compared to the spherical activated carbon;

(c) Material having a large specific surface area and a high volume of the micropore suitable for adsorption of small molecules such as uremic toxins can be expected to be made.

(d) Compared to the spherical activated carbon, the fiber has a highly uniform cross-sectional diameter (sometimes referred to hereinafter as "fiber diameter") (size);

(e) Compared to conventional spherical activated carbon, the fiber is finer (one-tenth or less in diameter), and can be expected to have a higher adsorption rate.

The ACFs in the present invention have a cross-sectional diameter of the fiber (average diameter) of 5 to 50 µm preferably, and more preferably 5 to 30 µm. The ACFs having a diameter of less than 5 µm are not preferred due to concerns about residual ACFs in vivo and cellular uptake although the amount and rate of adsorption increases. The ACFs having a diameter of more than 50 µm are not preferred since the rate of adsorption slows and the effect as an adsorbent for oral administration diminishes. The term "average diameter" as used in the present invention refers to a Dv50 value in the cross-sectional diameter of the fiber as described below.

The diameter can be varied depending on the fineness of the raw material fiber used and the degree of drawing and/or shrinking in intermediate treatment processes such as flame-proofing, and the degree of activation.

The ACFs of the present invention may be of any cross-sectional shape such as round, oval, chrysanthemum-shaped, and polygonal, depending on the cross-sectional shape of the raw material fiber used.

The ACFs in the present invention may have any fiber length. Preferably, the fiber length is 10 to 5000 µm and more preferably 15 to 3000 µm. The fiber length is still more preferably 20 to 3000 µm, and further preferably 90 to 3000 µm. The ACFs having a length of more than 5000 µm are not preferred since such ACFs gather together in bundles, and pill easily. For improving this problem, it is effective to shorten the fiber length. In order to shorten the fiber length, common grinders may be used. For example, a ball mill, a jet mill, or a mechanical rotary grinder can grind the fiber. Moreover, when the fibrous form is destroyed by grinding the resulting in lower adsorption ability, the particulate formed by destruction of the fiber may be removed through sieving or with a classifier. The adjustment of the fiber length is accomplished by shredding long fibers or subjecting long fiber, felt, or textile ACFs to grinding (milling). Certain treatments such as sieving can be carried out for equalizing the fiber length.

The ACFs in the present invention preferably have a specific surface area of 250 to 4000 m²/g, more preferably 800 to 4000 m²/g, and still more preferably 600 to 3500 m²/g. The ACFs having a specific surface area of less than 250 m²/g are not preferred since the adsorbed amount of uremic toxins decreases. The ACFs having a specific surface area of more than 4000 m²/g are not preferred since they have enlarged pores, thereby decreasing the adsorbed amount of low-molecular-weight substances such as uremic toxins, while increasing the adsorbed amount of beneficial high-molecular-weight substances, such as enzymes, resulting in a decrease in the selective adsorptivity toward uremic toxins. The specific surface area is preferably 900 to 3000 m²/g, still more preferably 1000 to 3000 m²/g, further preferably 1400 to 2700 m²/g, still more preferably 1400 to 2500 m²/g, and further preferably 1400 to 2200 m²/g.

The ACFs in the present invention preferably have a total pore volume of 0.2 to 3.0 mL/g and more preferably 0.4 to 2.0 mL/g. The ACFs having a total pore volume of less than 0.2 mL/g are not preferred since the amount of uremic toxins adsorbed decreases. The ACFs having a total pore volume of more than 3.0 mL/g are not preferred since they have enlarged pores, thereby decreasing the adsorbed amount of low-molecular-weight substances such as uremic toxins, while increasing the adsorbed amount of beneficial high-molecular-weight substances such as enzymes, resulting in a decrease in the selective adsorptivity toward uremic toxins. The total pore volume is more preferably 0.5 to 1.8 mL/g, still more preferably 0.8 to 1.8 mL/g, and further preferably 1.0 to 1.7 mL/g.

The ACFs in the present invention preferably has a micropore volume of 0.1 to 2.0 mL/g and more preferably 0.3 to 1.5 mL/g. The ACFs having a micropore volume of less than 0.1 mL/g are not preferred since the adsorbed amount of small molecules such as uremic toxins decreases. The micropore volume is still more preferably 0.5 to 1.0 mL/g, and further preferably 0.6 to 0.8 mL/g.

The ACFs in the present invention preferably have a mesopore volume of 0.8 mL/g or less, more preferably 0.7 mL/g or less, and still more preferably 0.5 mL/g or less. The ACFs having a mesopore volume of more than 0.8 mL/g are not preferred since the adsorbed amount of beneficial high-molecular-weight compounds such as enzymes increases.

The ACFs in the present invention preferably have a macropore volume of 0.3 mL/g or less, and more preferably 0.2 mL/g or less.

Any fiber that is commonly used as a raw material for producing ACFs can be used as a raw material for producing the ACFs in the present invention, such as polyacrylonitrile (PAN)-based, phenolic, pitch, rayon, cellulose, aramid, polyimide, polyamide, polyamideimide, polyphenylenebenzobisoxazole, polyvinyl alcohol, polysulphoneether, polysulphone, polyphenylene oxide, and lignin. In particular, polyacrylonitrile (PAN)-based, phenolic, pitch-based, and rayon-based ACFs are more preferred due to their superior adsorption performance and/or productivity.

The ACFs in the present invention can be produced by the following methods, for example but not limited thereto. Commercially available ACFs may also be used.

[Polyacrylonitrile (PAN)-Based ACF]

The Polyacrylonitrile (PAN)-based ACFs can be obtained by oxidizing polyacrylonitrile-based fibers in the air, followed by activation. The oxidation treatment is carried out at a temperature of 220 to 300° C. over 0.1 to 10 hours. The activation can include gas activation or chemical activation, and more preferred is gas activation. As the activating gas, steam and/or carbon dioxide, and even mixed gas composed of these gases and an inert gas such as nitrogen can be used.

[Phenolic ACF]

The phenolic ACFs can be obtained by activating phenol novolak fibers. If curing (oxidation) is previously carried out in a liquid phase system or gas phase system, the production of the phenolic ACFs does not involve the oxidation treatment that is required for the polyacrylonitrile-based ACFs, and may involve only curing.

[Pitch-Based ACF]

The pitch-based ACFs can be obtained by oxidizing fibers derived from petroleum- or coal-derived isotropic pitch material, followed by activation.

[Rayon-Based ACF]

The rayon-based ACFs can obtained by oxidizing rayon in the air, followed by activation.

The ACFs in the present invention can be used in a mixture with one another, or in a mixture or combination with a conventional known spherical activated carbon (for example, Kremezin (registered trademark)) as a therapeutic or prophylactic drug for kidney diseases or dialysis complications.

[Reactivation]

For the ACFs in the present invention, the ACFs as the raw material may be activated again (reactivation). Any type of ACFs as the raw material can be used, such as, for example, PAN-based, phenolic, pitch-based, and rayon-based ACFs. The ACFs having a specific surface area of 300 m²/g or more and preferably 500 to 2500 m²/g can be used for reactivation. The ACFs having a specific surface area of more than 2500 m²/g may increase the rate of reactivation so that it is difficult to control activation conditions. This may cause incineration, etc., and therefore a lower activation yield. The activation conditions (type of the activating gas, temperature, duration, etc.) are similar to those used in the production of ACFs as the raw material.

[Surface Desorption]

For reducing the number of surface functional groups in the ACFs, the ACFs in the present invention may be subjected to surface desorption by a heat treatment in an inert gas at 400 to 1200° C. at the late stage in the activation process of the ACFs or after the activation. In the heat treatment, a temperature of more than 1200° C. is not preferred since at the temperature, pores shrink to cause a decrease in the specific surface area, and therefore, preferred temperature is 1200° C. or less. The ACFs used in the heat treatment have any specific surface area, and preferred is 800 m²/g or more.

Any inert gas can be used, such as nitrogen, argon, and helium gases. Moreover, the heat treatment may be carried out with a reducing gas such as hydrogen gas at an ambient temperature to 500° C.

[Forms as Agents to be Administered]

The adsorbent for oral administration according to the present invention as a therapeutic or prophylactic drug for kidney diseases or dialysis complications comprises the above-mentioned ACFs as an active component. The dosage form can be powder, granule, tablet, sugar-coated tablet, capsule, suspension, stick, individual packaging, jelly or emulsion. When the adsorbent is used in the form of capsule, in addition to the conventional gelatin capsule, an enteric-coated capsule can be also used as needed. When the adsorbent is used in the form of tablet, the tablet is required to be disintegrated into the original fibrous form. The adsorbent may be used in the form of complex further compounded with other pharmaceutical agents such as lanthanum carbonate and sevelamer hydrochloride, or agents regulating electrolyte balance such as Kalimate and Kayexalate.

The adsorbent for oral administration according to the present invention can be used in any dosage form such as solid, semisolid, and liquid preparations.

A formulation according to the present invention is prepared using additives commonly used in pharmaceutical preparation. Those additives include excipients such as lactose, white soft sugar, glucose, corn starch, potato starch, microcrystalline cellulose, light anhydrous silicic acid, synthetic aluminum silicate, magnesium aluminometasilicate, and calcium hydrogen phosphate; binders such as microcrystalline cellulose, carboxymethyl cellulose, hydroxypropylcellulose, sodiun carboxymethyl cellulose, and polyvinyl pyrrolidone; disintegrants such as starch, sodiun carboxymethyl cellulose, carboxymethyl cellulose calcium, croscarmellose sodium, and sodium carboxymethyl starch; lubricants such as talc and stearic acid; coating agents such as hydroxymethylpropylcellulose, hydroxypropylmethyl cellulose phthalate, and ethyl cellulose; and coloring agents for the solid preparation; bases such as white petrolatum for the semisolid preparation, and, solvents such as ethanol, solubilizers such as ethanol, preservatives such as p-hydroxybenzoic esters, isotonizing agents such as glucose, buffering agents such as citric acid, antioxidants such as L-ascorbic acid, chelating agents such as EDTA, and suspending agents/emulsifying agents such as polysorbate 80 for the liquid preparation.

The dose of an active component in the adsorbent for oral administration according to the present invention is usually about 1 to 3000 mg/day, more preferably about 1 to 1000 mg/day, and the dose frequency is usually once to 3 times/day. On the other hand, for the adsorbents for oral administration comprising conventional spherical activated carbon, the dose is usually about 6000 mg/day.

[Forms as Beverage and Food Products and Food Additives]

The adsorbent for oral administration according to the present invention can not only be used as a pharmaceutical uremic toxin adsorbent but also can be applied to use in the form where the adsorbent is contained in a beverage and food product or food additive, that is, as a uremic-toxin adsorbing beverage and food product or food additive. In order to provide the beverage and food product or food additive compounded with an adsorbent for oral administration according to the present invention, the adsorbent may be compounded in an appropriate amount in the form of powder or liquid depending to the type or form of the base beverage and food product or food additive. The beverage and food products into which the adsorbent is compounded include, for example, conventional solid food products (for example, biscuit, bread, and noodle), liquid food products (for example, soft drink, and health drink), and semi-liquid food products (for example, custard pudding, and jelly), and the food additives into which the adsorbent is compounded include, for example, conventional preservatives, antioxidants, sweeteners, colorants, emulsifying agents, seasonings, spices, and acidulants.

[Indications]

The kidney diseases can include, for example, chronic kidney disease, acute renal failure, chronic pyelonephritis, acute pyelonephritis, chronic glomerulonephritis, rapidly progressive nephritic syndrome, nephrotic syndrome, nephrosclerosis, interstitial nephritis, diabetic nephropathy, focal glomerulosclerosis, membranous nephropathy, polycystic kidney syndrome, renovascular hypertension, and hypertension syndrome, as well as secondary kidney diseases associated with the above-mentioned primary diseases (Non-patent Literature 10). In addition, hyperphosphatemia, hyperkalemia, hyperuricemia, and hypernatremia accompanying chronic kidney disease can be included in kidney diseases in a broad sense.

The dialysis complications include, for example, pruritus, anemia, restless legs syndrome, cardiac failure, arteriosclerosis, dialysis amyloidosis, hyperphosphatemia, hyperkalemia, and pulmonary edema.

The activated carbon fibers according to the present invention are excellent in adsorptivity toward the uremic toxins in vivo such as indoxylsulfuric acid, indole, indoleacetic acid, guanidinoacetic acid, p-cresol, hippuric acid, furandicarboxylic acid, and homocysteine, as well as low-molecular-weight substances such as precursors thereof. Moreover, the activated carbon fibers have a beneficial selective adsorptivity, wherein the absorptivity toward substances beneficial for living organism, such as digestive enzymes (for example, amylase, trypsin, and lipase) is low.

The term "uremic toxin" as used in the present invention refers to a harmful toxic substance that is responsible for uremia, including, in addition to uremic toxins themselves, precursors thereof.

The adsorbent for oral administration according to the present invention can hardly causes side effects such as constipation that would be caused by high doses, is excellent at adsorbing low-molecular-weight organic compounds that is a causative agent for uremia, shows sufficient adsorption performance even in low doses, and suppresses adsorption of high-molecular-weight compounds such as enzymes essential to living organism.

Therefore, the adsorbent according to the present invention is effective as an adsorbent for oral administration, in particular, for patients presenting with pathological conditions such as chronic kidney disease in which toxins are accumulated in vivo.

In this application, measurement methods of physical properties are as follows:

(A) Cross-Sectional Diameter of the Fiber

The cross-sectional diameter of the fiber (fiber diameter) was calculated by the following method. Using an image analysis-based particle size/shape distribution measurement instrument PITA-II (from SEISHIN ENTERPRISE Co., LTD.) with a 4-times magnification lens, a total of 4000 to 8000 fiber shapes were measured by repeating multiple measurements.

The numerical value obtained by dividing the "area" of the fiber imaged by the measurement instrument by "skeleton length" (the length obtained after the resulting image is subjected to thinning process) was defined as the fiber diameter of the fiber.

The volume of the fiber was calculated according to the equation $V=\pi(A/2)^2 \times B$, wherein V represents the volume of the fiber, A represents the fiber diameter, and B represents the fiber length. The data for individual fibers are arranged in the order of increasing fiber diameter, the volume of each fiber is added in ascending order of the fiber diameter, and the fiber diameters when the sum reaches 10%, 50%, and 90% of the total volume were defined as cumulative 10%, 50%, and 90% of the fiber diameter (hereinafter, Dv10, Dv50, and Dv90), respectively. The value Dv50 calculated was defined as the cross-sectional diameter of the fiber (average diameter).

On the other hand, for commercially available ACFs, the fiber diameters published by the manufacturers as the product specifications were shown.

(B) Fiber Length

The length of the fiber was calculated by the following method. Using an image analysis-based particle size/shape distribution measurement instrument PITA-II (from SEISHIN ENTERPRISE Co., LTD.) with a 4-times magnification lens, a total of 4000 to 8000 fiber shapes were measured by repeating multiple measurements.

The "maximum length" of the fiber imaged by the measurement instrument was defined as the length of the fiber.

The volume of the fiber was calculated according to the equation $V=\pi(A/2)^2 \times B$, wherein V represents the volume of the fiber, A represents the fiber diameter, and B represents the fiber length. The data for individual fibers are arranged in the order of increasing length of the fiber, the volume of each fiber is added in ascending order of the length of the fiber, and the lengths of the fiber when the sum reaches 10%, 50%, and 90% of the total volume were defined as cumulative 10%, 50%, and 90% of the length of the fiber (hereinafter, Dv10, Dv50, and Dv90) respectively. The value Dv50 calculated was defined as the length of the fiber (average length).

(C) Specific Surface Area (BET Method)

Using a specific surface area/pore size distribution measurement instrument (AUTOSORB-1 from Quantachrome), the amount of gas adsorbed by the ACF is measured to determine the specific surface area from the BET equation. Specifically, the sample ACF was allowed to adsorb nitrogen at −196° C. and a relationship between the nitrogen partial pressure and the amount of adsorption (an adsorption isotherm) was measured.

[Expression 1]

$$\frac{1}{W \cdot ((P_0/P) - 1)} = \frac{1}{Wm \cdot C} + \frac{C-1}{Wm \cdot C}\left(\frac{P}{P_0}\right) \quad \text{BET equation (1)}$$

W: The amount of nitrogen adsorbed at a relative pressure $(P/P_0)$ (g)
Wm: The amount of nitrogen when covered with a monomolecular layer (g)
C: BET constant Using the data in a range where relative pressure $(P/P_0)$ is 0.05 to 0.35 in the adsorption isotherm, plotting (BET plotting) of $P/P_0$ and $1/W$ $(P_0/P-1)$ was carried out. The amount of nitrogen adsorbed on the monomolecular layer (Wm (g)) was calculated with the gradient of the BET plot (s) and the intercept (i).

[Expression 2]

From BET equation (1) $S=(C-1)/(WmC)$ (2)

$i=1/(WmC)$ (3)

From (2) and (3) $Wm=1/(s+i)$ (4)

Total surface area $St(m^2)=WmNAcs/M$ (5)

N: Avogadro's number $(6.023 \times 10^{23}/\text{mol})$
M: Molecular weight of nitrogen
Acs: Cross sectional area of nitrogen molecule (16.2 Å)

(D) Pore Volume

As in the case of the measurement method of the specific surface area, the pore volume was determined from the adsorption isotherm of nitrogen by using density functional theory.

Total pore volume: calculated from the total amount of the gas adsorbed at a relative pressure of near 1, assuming that pores are filled with liquid nitrogen.

Micropore volume: Fiest, a pore having a pore size diameter of 20 Å or less is defined as a micropore. Then, the pore volume of the pores having the diameter 20 Å or less was calculated from the pore size obtained from the adsorption isotherm and the cumulative curve of pore volume.

Mesopore volume: A pore having a pore size diameter of 20 to 100 Å is defined as a mesopore. The pore volume was calculated from the pore size obtained from the adsorption isotherm and the cumulative curve of pore volume.

Macropore volume: determined by subtracting the micropore volume and the mesopore volume from the total pore volume.

EXAMPLES

The present invention will now be particularly described in the following examples, which do not limit the scope of the invention. In the measurement of physical properties and evaluation of adsorption performance of ACFs prepared in Examples, fibers having a long fiber length were removed. The remaining fibers were subjected to grinding, followed by screening through sieves having a mesh size of 150 μm, 75 μm, 38 μm, and 20 μm, and materials that remained on respective sieves having a mesh size of 75 μm, 38 μm, and 20 μm were collected and used, for facilitating the measurement operation or administration to animals.

Example 1

Polyacrylonitrile-based ACFs (fiber diameter 9 μm: trade name "FINEGARD: FW-510" from Toho Kako Kensetsu) were used. The properties of the ACFs are shown in Table 1.

Example 2

Phenolic ACFs (fiber diameter 15 μm: trade name "KURACTIVE" from KURARAY CHEMICAL CO., LTD.) were used. The properties of the ACFs are shown in Table 1, the measured fiber lengths in Table 2, and the fiber length distribution in FIG. 3.

Example 3

Phenolnovolak fibers (fiber diameter 17 μm: trade name "KYNOL" from Gun Ei Chemical Industry Co., Ltd.) were activated with steam at 950° C. for 120 minutes to obtain ACFs of the present invention. The properties of the resulting ACFs are shown in Table 1.

Example 4

Pitch-based ACFs (fiber diameter 15 μm: trade name "A-15" from AD'ALL) were used. The properties of the ACFs are shown in Table 1.

Example 5

Oxidized polyacrylonitrile-based fibers (fiber diameter 14 μm: trade name "Pyromex" from TOHO TENAX Co., Ltd.)

were activated with steam at 950° C. for 60 minutes to obtain ACFs of the present invention. The properties of the resulting ACFs are shown in Table 1.

Example 6

Phenolic ACFs (fiber diameter 15 μm: trade name "KURACTIVE" from KURARAY CHEMICAL CO., LTD.) were heated to 900° C. under a stream of nitrogen and, after the replacement of nitrogen by steam, activated with steam for 60 minutes. In the temperature-falling process after the completion of activation, the reaction was stopped again under a stream of nitrogen to obtain ACFs of the present invention. The properties of the ACFs are shown in Table 1.

Example 7

Phenolic ACFs (fiber diameter 15 μm: trade name "KURACTIVE" from KURARAY CHEMICAL CO., LTD.) were heated to 900° C. under a stream of nitrogen, followed by surface desorption for 120 minutes. In the temperature-falling process from the preset temperature, while still introducing nitrogen gas, the reaction was stopped to obtain ACFs of the present invention. The properties of the ACFs are shown in Table 1.

Example 8

Phenolic ACFs (fiber diameter 15 μm: trade name "KURACTIVE" from KURARAY CHEMICAL CO., LTD.) were heated to 800° C. under a stream of nitrogen, followed by surface desorption for 30 minutes. In the temperature-falling process from the preset temperature, while still introducing nitrogen gas, the reaction was stopped to obtain ACFs of the present invention. The properties of the ACFs are shown in Table 1.

Example 9

Oxidized polyacrylonitrile-based fibers (fiber diameter 14 μm: trade name "Pyromex" from TOHO TENAX Co., Ltd.) were activated with steam at 950° C. for 70 minutes to obtain ACFs of the present invention. The properties of the resulting ACFs are shown in Table 1.

Example 10

The ACFs prepared in Example 2 were subjected to classification using a circulating air flow sieving measurement instrument with a sieve having a mesh size of 10 μm after grinding. Materials that passed through the sieve were collected to obtain ACFs having a short fiber length. The properties of the ACFs are shown in Table 1, the measured fiber lengths in Table 2, and the fiber length distribution in FIG. 4.

Example 11

Phenolic ACFs (fiber diameter 16 μm: trade name "KURACTIVE" from KURARAY CHEMICAL CO., LTD.) were used. The properties of the ACFs are shown in Table 1.

Example 12

Phenolnovolak fibers (fiber diameter 12 μm: trade name "KYNOL" from Gun Ei Chemical Industry Co., Ltd.) were activated with steam at 900° C. for 50 minutes to obtain ACFs of the present invention. The properties of the ACFs are shown in Table 1, and the measured cross-sectional diameters of the fibers in Table 3.

Example 13

Phenolnovolak fibers (fiber diameter 38 μm: trade name "KYNOL" from Gun Ei Chemical Industry Co., Ltd.) were activated with steam at 900° C. for 50 minutes to obtain ACFs of the present invention. The properties of the ACFs are shown in Table 1, and the measured cross-sectional diameters of the fibers in Table 3.

Example 14

Phenolnovolak fibers (fiber diameter 17 μm: trade name "KYNOL" from Gun Ei Chemical Industry Co., Ltd.) were activated with steam at 500° C. for 10 minutes to obtain ACFs of the present invention. The specific surface area of the ACF was less than 600 m$^2$/g.

Example 15

Pitch-based ACFs (fiber diameter 15 μm: trade name "A-20" from AD'ALL) were used. The properties of the ACFs are shown in Table 1.

Example 16

Rayon fibers (fiber diameter 31 μm) were treated with an aqueous ammonium phosphate solution, followed by oxidation treatment in air at 270° C. for 2 hours, and then activation was carried out with steam at 900° C. for 50 minutes to obtain ACFs of the present invention. The properties of the ACFs are shown in Table 1.

Example 17

Phenolic ACFs (fiber diameter 15 μm: trade name "KURACTIVE" from KURARAY CHEMICAL CO., LTD.) were heated to 900° C. under a stream of nitrogen and, after the replacement of nitrogen by steam, activated with steam for 120 minutes. In the temperature-falling process after the completion of activation, the reaction was stopped again under a stream of nitrogen to obtain the ACFs of the present invention. The properties of the ACFs are shown in Table 1.

Example 18

Phenolnovolak fibers (fiber diameter 17 μm: trade name "KYNOL" from Gun Ei Chemical Industry Co., Ltd.) were activated with steam at 900° C. for 10 minutes to obtain ACFs of the present invention. The properties of the ACFs are shown in Table 1.

Comparative Example 1

KREMEZIN (registered trademark, KUREHA CORPORATION "KREMEZIN Fine Granule") was used.

For the respective ACFs prepared in Examples 1 to 13 and 15 to 18, and spherical activated carbon in Comparative Example 1, certain physical properties, i.e. specific surface area and pore volume (total pore volume, micropore volume, mesopore volume, and macropore volume) were measured. These results are shown in Table 1.

TABLE 1

| | Specific surface area (m²/g) | Total pore volume (mL/g) | Micropore volume (mL/g) | Mesopore volume (mL/g) | Macropore volume (mL/g) |
|---|---|---|---|---|---|
| Comparative Example 1 | 1400 | 0.83 | 0.51 | 0.25 | 0.07 |
| Example 1 | 1440 | 1.08 | 0.43 | 0.60 | 0.05 |
| Example 2 | 1420 | 0.81 | 0.66 | 0.05 | 0.10 |
| Example 3 | 2190 | 1.45 | 0.79 | 0.45 | 0.21 |
| Example 4 | 1240 | 0.70 | 0.48 | 0.20 | 0.05 |
| Example 5 | 1300 | 0.81 | 0.44 | 0.30 | 0.10 |
| Example 6 | 1935 | 1.30 | 0.76 | 0.39 | 0.14 |
| Example 7 | 1467 | 1.01 | 0.62 | 0.24 | 0.15 |
| Example 8 | 1520 | 1.00 | 0.64 | 0.24 | 0.11 |
| Example 9 | 2098 | 1.38 | 0.63 | 0.66 | 0.10 |
| Example 10 | 1132 | 0.81 | 0.48 | 0.19 | 0.14 |
| Example 11 | 843 | 0.61 | 0.37 | 0.18 | 0.06 |
| Example 12 | 1483 | 1.05 | 0.63 | 0.26 | 0.16 |
| Example 13 | 1362 | 0.91 | 0.59 | 0.24 | 0.09 |
| Example 15 | 1887 | 1.11 | 0.57 | 0.46 | 0.08 |
| Example 16 | 1164 | 0.76 | 0.49 | 0.19 | 0.08 |
| Example 17 | 2642 | 1.62 | 0.72 | 0.74 | 0.15 |
| Example 18 | 658 | 0.49 | 0.32 | 0.12 | 0.05 |

TABLE 2

| | Fiber length (μm) | | |
|---|---|---|---|
| | Dv10 | DV50 | Dv90 |
| Example 2 | 90.4 | 190.1 | 336.4 |
| Example 10 | 7.1 | 12.0 | 17.7 |

TABLE 3

| | Cross-sectional diameter of the fiber (μm) | | |
|---|---|---|---|
| | Dv10 | DV50 | Dv90 |
| Example 12 | 9.8 | 11.2 | 13.1 |
| Example 13 | 23.5 | 29.8 | 37.0 |

The following evaluation of adsorption performance for ACFs prepared in Examples in order to compare the adsorption performance with a conventional adsorbent for oral administration.

[Evaluation of Uremic Toxin Adsorption Performance in the Dietary Components]

In order to measure the uremic toxin adsorption performance of the adsorbent for oral administration according to the present invention under conditions reflecting the state in which food is present in the digestive tract that is assumed to be a site at which an adsorbent exerts its activity, and to compare adsorption performance with the conventional adsorbent for oral administration, the adsorption performance in Ensure Liquid, an enteral nutrient (semidigest diet nutrient), was measured for the adsorbent for oral administration according to the present invention. In Comparative Example 1, KREMEZIN (registered trademark, KUREHA CORPORATION "KREMEZIN Fine Granule"), a therapeutic drug for chronic renal failure comprising spherical activated carbon, was used. The adsorption performance toward indoleacetic acid was measured by the following method over time.

The ACFs of Example 1 to 10 and the spherical activated carbon of Comparative Example 1 were dried at 115° C. for 4 hours, and 25 mg of each of the samples was precisely weighed into separate polypropylene tubes. A uremic toxin (indoleacetic acid) was dissolved in Ensure Liquid (from Abbott) to make a concentration of 80 μg/mL, and 10 mL of the resultant solution was added to the above-mentioned polypropylene tubes. The mixture was shaken at 37° C., and a part of the supernatant of the mixture was collected in 1, 3, 5, and 24 hours. Then, deproteinization (acetonitrile precipitation) was carried out using acetonitrile, the concentration of the uremic toxin in the solution after the deproteinization was determined by liquid chromatograph-mass spectrometry (LC-MS). The adsorptivity was calculated from the concentration of the uremic toxin obtained by liquid chromatograph-mass spectrometry, assuming adsorptivity in the case of the concentration of the uremic toxin in the absence of any adsorbent as 0% and adsorptivity in the absence of the uremic toxin in the solution as 100%. The adsorption rate was expressed as the time period (h) required to adsorb 50%, assuming the amount of adsorption in 24 hours as 100%. These results are shown in Table 4 and FIG. 1.

TABLE 4

| | Adsorption rate (h) | Adsorptivity (%) |
|---|---|---|
| Comparative Example 1 | 11.18 | 63.4 |
| Example 1 | 1.51 | 88.1 |
| Example 2 | 1.35 | 86.4 |
| Example 3 | 1.03 | 86.0 |
| Example 4 | 1.55 | 88.3 |
| Example 5 | 0.73 | 98.8 |
| Example 6 | 0.46 | 83.8 |
| Example 7 | 0.43 | 81.8 |
| Example 8 | 0.66 | 70.3 |
| Example 9 | 1.22 | 98.7 |
| Example 10 | 7.7 | 55.6 |

As shown in Table 4 and FIG. 1, the ACFs of the present invention have much higher adsorption rates and higher adsorptivity for various ACFs from different raw materials, compared to the spherical activated carbon of Comparative Example 1. That is, the ACFs of the present invention can adsorb indoleacetic acid, a uremic toxin, rapidly, greatly, and persistently in an organic solution similar to the state in which food is present in the digestive tract.

Accordingly, the adsorbents for oral administration comprising ACFs of the present invention have a greatly superior uremic toxin adsorption performance compared to the adsorbent for oral administration comprising conventional spherical activated carbon.

Figure 3:
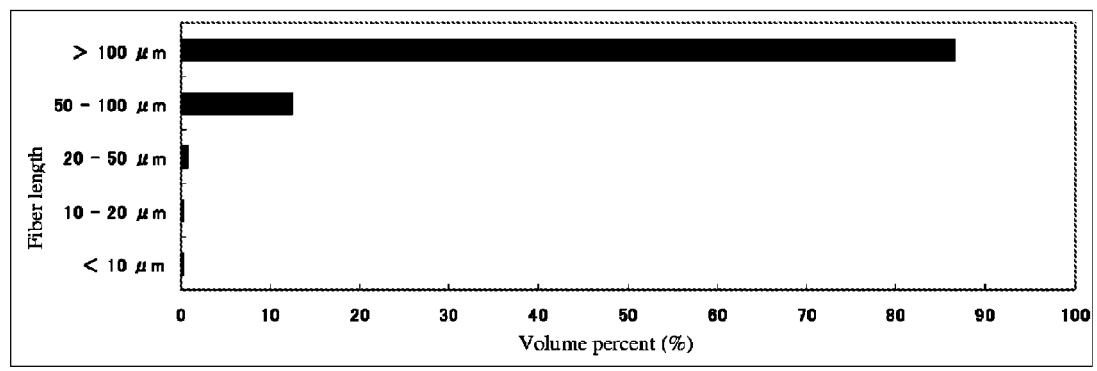
FIG. 3 is a graph showing the distribution of the fiber length of the ACFs after grinding in Example 2.
Figure 4:
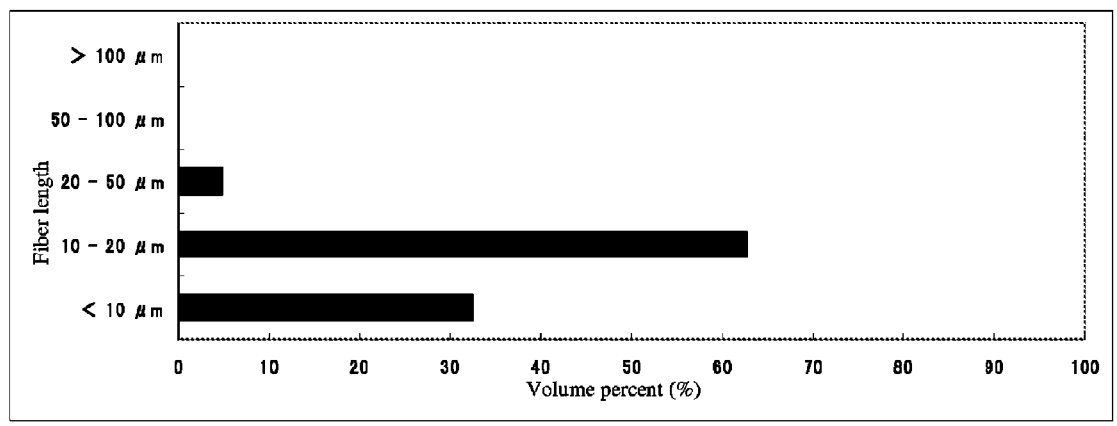
FIG. 4 is a graph showing the distribution of the fiber length of the ACFs in Example 10.

Moreover, as shown in Tables 2 and 4, and FIGS. 3 and 4, the ACFs of Example 10 formed by collecting ones having a short fiber length out of the ACFs of Example 2 has a much lower uremic toxin adsorption performance than that of ACFs of Example 2. Based on these results, it is believed that the shape of a fiber in which the length is larger than the cross-sectional diameter, which is characteristic of fibers, is important for exhibiting a high adsorption performance. The adsorbents for oral administration comprising fibrous activated carbon have a superior adsorption performance to the adsorbents for oral administration comprising conventional spherical activated carbon.

[Evaluation of the Effect of Reducing the Serum Levels of Uremic Toxin in a Normal Mouse]

For each of the ACFs prepared in Examples 2, 3, 6, 7, 11 to 18, and the spherical activated carbon in Comparative Example 1, the effect of reducing the serum levels of uremic toxin in the case of oral administration to mice was evaluated. Male mice ICR, 8-9 weeks old, (CHARLES RIVER LABORATORIES JAPAN, INC., Japan SLC, Inc.) were divided into a vehicle treatment group, a Comparative Example treatment group and an Example treatment group (n=6 to 7) based on the body weight of mice so that there showed no bias in the body weight among groups. In the Comparative Example treatment group, the spherical activated carbon was administered at a dose of 5 mg, 15 mg, or 30 mg once daily to mice, while in the Example treatment group, the ACF was administered at a dose of 5 mg by gavage to mice. In one week after administration, blood was collected from abdominal aorta in the mice under anesthesia. After deproteinization of the collected serum with 85% acetonitrile, the serum levels of indoxylsulphuric acid were measured by LC-MS/MS (API4000 LC-MS/MS). In order to clearly show the activity strength between Comparative Example and Examples, the difference in the average value of the serum levels of indoxylsulphuric acid between each group and the vehicle treatment group was divided by the average value of the serum levels of indoxylsulphuric acid of the vehicle treatment group to calculate the reduction rate (%). These results are shown in Table 5 and FIG. 2.

TABLE 5

|  | Dose (mg/head) | Reduction rate (%) |
|---|---|---|
| Comparative Example 1 | 5 | 1.4 |
| Comparative Example 1 | 15 | 14.2 |
| Comparative Example 1 | 30 | 35.5 |
| Example 2 | 5 | 44.0 |
| Example 3 | 5 | 56.8 |
| Example 6 | 5 | 61.0 |
| Example 7 | 5 | 48.3 |
| Example 11 | 5 | 26.5 |
| Example 12 | 5 | 51.7 |
| Example 13 | 5 | 49.5 |
| Example 15 | 5 | 59.3 |
| Example 16 | 5 | 56.5 |
| Example 17 | 5 | 19.4 |
| Example 18 | 5 | 16.6 |

Figure 2:
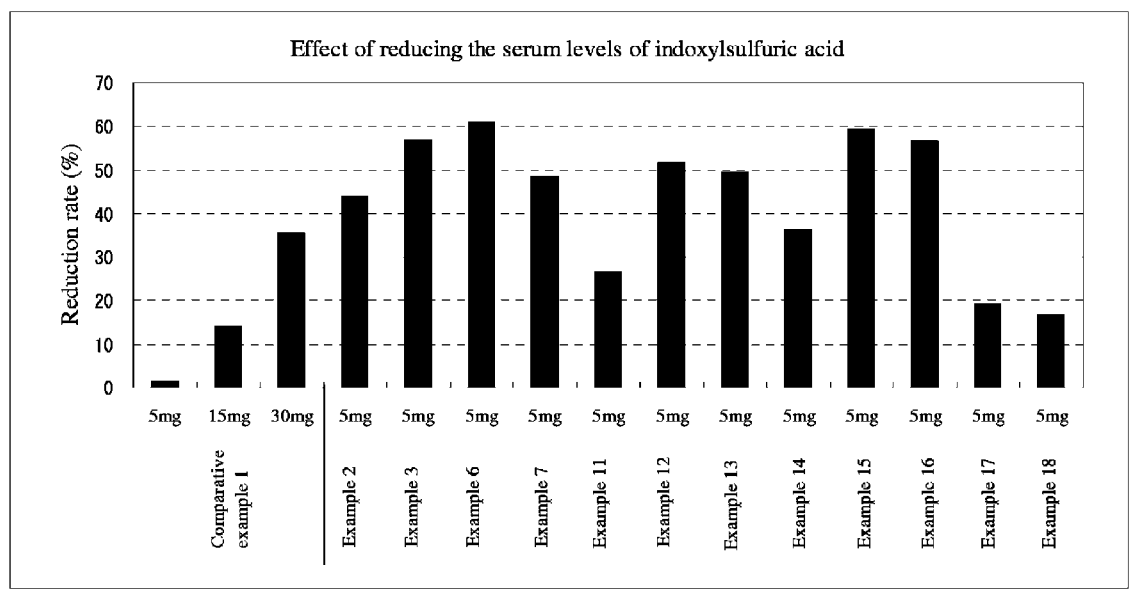
FIG. 2 is a graph showing the effect of reducing the serum uremic toxin level in a normal mouse for Examples.

In a comparison between the ACFs of the present invention and the spherical activated carbon of Comparative Example 1, as shown in Table 5 and FIG. 2, the ACFs of the present invention at a dose of 5 mg showed a high effect of reducing the serum levels of indoxylsulfuric acid for various ACFs from different raw materials while the spherical activated carbon of Comparative Example 1 hardly showed such an effect at the same dose. Moreover, the ACFs of the present invention at a dose of 5 mg showed a higher effect of reducing the serum levels of indoxylsulfuric acid for ACFs of Examples 11, 17 and 18 than that when the spherical activated carbon of Comparative Example 1 was administered at a dose of 15 mg, and the other ACFs showed a higher effect of reducing the serum levels of indoxylsulfuric acid than that when the spherical activated carbon of Comparative Example 1 was administered at a dose of 30 mg. Accordingly, the adsorbents for oral administration comprising ACFs of the present invention are quite excellent in that the adsorbents have a greatly superior uremic toxin adsorptive activity compared to the adsorbents for oral administration comprising conventional spherical activated carbon, and can solve the problem of high doses associated with the adsorbents for oral administration comprising conventional spherical activated carbon.

INDUSTRIAL APPLICABILITY

The adsorbents for oral administration according to the present invention can be used for treating or preventing kidney diseases or dialysis complications.

The invention claimed is:

1. A method for adsorbing a uremic toxin comprising oral administration of activated carbon fiber to a subject in need thereof;
   wherein when the activated carbon fiber is a rayon-based activated carbon fiber, the diameter of the rayon-based activated carbon fiber is at least 9 μm.
2. The method according to claim 1, wherein the activated carbon fibers have a micropore volume of 0.1 to 2.0 mL/g.
3. The method according to claim 1, wherein the activated carbon fibers have a fiber length of 15 μm or more and a micropore volume of 0.5 to 1.0 mL/g.
4. The method according to claim 1 whereby kidney diseases or dialysis complications are treated or prevented.
5. The method according to claim 1, wherein the adsorbent is administered at a daily dose of 1 to 3000 mg.
6. A method for adsorbing a uremic toxin comprising oral administration of activated carbon fiber to a subject in need thereof; wherein the activated carbon fiber has a cross-sectional diameter of the fiber of 5 to 50 μm, a fiber length of 15 μm or more, a specific surface area as determined by BET method of 1400 to 2700 $m^2/g$, a total pore volume of 0.8 to 1.8 mL/g, and a micropore volume of 0.5 to 1.0 mL/g; wherein when the activated fiber is a rayon-based activated carbon fiber, the diameter of the rayon-based activated carbon fiber is at least 9 μm.

* * * * *